United States Patent
Olson et al.

(10) Patent No.: US 7,704,589 B2
(45) Date of Patent: Apr. 27, 2010

(54) ABSORBENT GARMENT WITH COLOR CHANGING FIT INDICATOR

(75) Inventors: Christopher Peter Olson, Neenah, WI (US); Lawrence Howell Sawyer, Neenah, WI (US); Robert Lee Popp, Hortonville, WI (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 734 days.

(21) Appl. No.: 10/955,239

(22) Filed: Sep. 30, 2004

(65) Prior Publication Data

US 2006/0068168 A1 Mar. 30, 2006

(51) Int. Cl.
*A61F 13/15* (2006.01)
(52) U.S. Cl. .................. 428/152; 428/179; 428/181; 604/358; 604/385.01
(58) Field of Classification Search .............. 428/141, 428/152, 179, 181; 604/356, 361, 385.24, 604/385.25, 385.26, 385.27, 385.28, 385.29, 604/385.3, 358, 385.01
See application file for complete search history.

(56) References Cited

U.S. PATENT DOCUMENTS

| | | | |
|---|---|---|---|
| 4,100,324 A | | 7/1978 | Anderson et al. |
| 4,231,370 A | | 11/1980 | Mroz et al. |
| 4,662,875 A | * | 5/1987 | Hirotsu et al. .......... 604/389 |
| 4,663,220 A | | 5/1987 | Wisneski et al. |
| 4,704,116 A | | 11/1987 | Enloe |

(Continued)

FOREIGN PATENT DOCUMENTS

WO    WO9851247 A1    11/1998

(Continued)

OTHER PUBLICATIONS

Article—*Optomechanical properties of stretched polymer dispersed liquid crystal films for scattering polarizer applications*, Ichiro Amimori, Nikolai V. Priezjev, Robert A. Pelcovits, and Gregory P. Crawford, Journal of Applied Physics, vol. 93, No. 6, Mar. 15, 2003, pp. 3248-3252.

(Continued)

*Primary Examiner*—Alicia Chevalier
(74) *Attorney, Agent, or Firm*—Dority & Manning P.A.

(57) ABSTRACT

An absorbent article having a built-in size indicator is disclosed. The size indicator, for instance, comprises a stretchable panel that changes color when stretched. The panel may change color to indicate that the article is the correct size for the wearer or may change color to indicate that the article is too small. Still another embodiment, the stretchable panel may change from a first color indicating that the article is too large, to a second color that indicates the article is the correct size, and to a third color that indicates the article is too small. The stretchable panel may be made from any suitable color changing materials. For example, in one embodiment, the panel may include a gathered layer that is printed with a particular color only at the peaks of the gathered layer. As the gathered material is stretched, the material changes color due to the newly exposed regions. In other embodiments, the stretchable panel comprises a film that changes color when stretched. For example, the film may comprise a polyethylene that crystallizes when stretched or may comprise a polarized film that increases in polarization when stretched.

39 Claims, 9 Drawing Sheets

U.S. PATENT DOCUMENTS

| | | | |
|---|---|---|---|
| 4,720,415 A | 1/1988 | Vander Wielen et al. | |
| 4,734,320 A * | 3/1988 | Ohira et al. | 428/40.1 |
| 4,905,851 A | 3/1990 | Thompson | |
| 4,940,464 A | 7/1990 | Van Gompel et al. | |
| 5,046,272 A | 9/1991 | Vogt et al. | |
| 5,104,116 A | 4/1992 | Pohjola | |
| 5,221,274 A * | 6/1993 | Buell et al. | 604/385.3 |
| 5,224,405 A | 7/1993 | Pohjola | |
| 5,226,992 A | 7/1993 | Morman | |
| 5,284,703 A | 2/1994 | Everhart et al. | |
| 5,336,422 A | 8/1994 | Scheinbeim et al. | |
| 5,350,624 A | 9/1994 | Georger et al. | |
| 5,389,093 A | 2/1995 | Howell | |
| 5,486,166 A | 1/1996 | Bishop et al. | |
| 5,490,846 A | 2/1996 | Ellis et al. | |
| 5,613,302 A | 3/1997 | Berman et al. | |
| 5,645,542 A | 7/1997 | Anjur et al. | |
| 5,820,973 A | 10/1998 | Dodge, II et al. | |
| 6,049,428 A | 4/2000 | Khan et al. | |
| 6,174,394 B1 | 1/2001 | Gvon et al. | |
| 6,297,424 B1 | 10/2001 | Olson et al. | |
| 6,362,389 B1 | 3/2002 | McDowall et al. | |
| 6,563,640 B1 | 5/2003 | Ignatov et al. | |
| 6,583,284 B1 | 6/2003 | Sidorenko et al. | |
| 6,645,190 B1 | 11/2003 | Olson et al. | |
| 6,761,711 B1 | 7/2004 | Fletcher et al. | |
| 2002/0062117 A1 * | 5/2002 | Raufman et al. | 604/389 |
| 2002/0104608 A1 | 8/2002 | Welch et al. | |
| 2003/0161022 A1 | 8/2003 | Lazarev et al. | |
| 2005/0143699 A1 * | 6/2005 | Linder | 604/383 |

FOREIGN PATENT DOCUMENTS

| | | | | |
|---|---|---|---|---|
| WO | WO 00/20178 | * | 4/2000 | 264/474 |
| WO | WO2005037159 A1 | | 4/2005 | |

OTHER PUBLICATIONS

Translation of Japanese Patent No. JP60194947, 8 pages, Oct. 3, 1985.

Search Report and Written Opinion for PCT/US2005/023663, Oct. 26, 2005.

* cited by examiner

ABSORBENT GARMENT WITH COLOR CHANGING FIT INDICATOR

BACKGROUND OF THE INVENTION

Absorbent articles such as diapers, training pants, incontinence garments, swim pants, fitted briefs and the like conventionally include a liquid permeable body-facing liner, a liquid impermeable outer cover, and an absorbent core. The absorbent core is typically located in between the outer cover and the liner for taking in and retaining liquids (e.g., urine) exuded by the wearer.

In some of these absorbent articles, the articles contain various elastic materials to permit some expansion of the article when necessary and/or to provide a better fit on the wearer. For example, some absorbent articles have been made in the past containing waist elastic members that allow the waist of the article to expand and contract. Absorbent articles have also been made with side elastic members that allow the articles to expand around the hip of a wearer. The elastic components not only provide the article with some form-fitting properties but also allow the article to accommodate a range of sizes.

Although some absorbent articles allow for a wide range of fit, problems still persist in consumers buying articles that are not technically the correct size for the wearer. For example, consumers may attempt to save money by buying a smaller size product, or, instead, may purchase a larger size product in order to have extra absorbency. In other cases, a parent may not know the exact weight of their child and purchase the wrong size.

Although some products made in the past may accommodate some variety of sizes, a need exists for a garment that includes a size indicator. Specifically, a need exists for a garment that is capable of indicating to the user whether the garment is too small for the wearer once the garment is placed on the wearer. A need also exists for a fit indicating garment that is capable of indicating when the garment is too big for a wearer once placed on the wearer.

SUMMARY OF THE INVENTION

In general, the present invention is directed to disposable absorbent articles that have a built-in visual fit indicator. Through the visual indicator, the absorbent articles of the present invention are capable of indicating to a wearer when the fit is too small, when the fit is too big, and/or when the fit is just right.

For example, in one embodiment, an absorbent article made according to the present invention includes a chassis defining a waist opening opposite two leg openings. The chassis comprises an outer cover, a bodyside liner, and an absorbent structure positioned in between the outer cover and the bodyside liner.

At least one stretchable panel is associated with the article. For example, the stretchable panel is associated with the article by being attached to the article or being integral with the article. The stretchable panel is positioned to stretch when the absorbent article is being placed on a wearer. In accordance with the present invention, the stretchable panel changes color when the panel is stretched beyond a certain percentage indicating to the user that the article is approaching a size limit. As used herein, a color change refers to a change in hue and/or saturation as opposed to merely a change in brightness. The stretchable panel may be secured to an exterior surface of the chassis or may be integral with the chassis. The stretchable panel may be, for instance, a side region, a waist panel, a band that circumscribes the hip circumference of the article or may comprise the entire chassis. In one embodiment, the stretchable panel may be elastic for also providing the article with form-fitting properties.

As described above, in one embodiment, the stretchable panel may change from a first color to a second color when stretched beyond a certain percentage. In an alternative embodiment, however, the stretchable panel may be configured to change from a first color, to a second color and then to a third color as the panel is stretched. For example, the stretchable panel may exhibit a first color when in a substantially relaxed state. As the panel is stretched within a first percentage range, the panel may change a second color and then change to a third color when stretched even further to a second percentage range. In this embodiment, the first color may indicate to the wearer that the absorbent article is too large, the second color may indicate that the absorbent article is the correct size, and the third color may indicate that the article is approaching a size limit and may be too small.

In addition to or instead of changing color, the stretchable panel can also be configured to undergo a pattern change when stretched. For example, in one embodiment, the stretchable panel can contain discrete shapes that turn into lines or linear rows when stretched. In another embodiment, various graphics may be printed on the stretchable panel that change in their appearance to indicate either that the garment fits correctly or that the garment is too small. In this embodiment, any suitable graphics capable of changing shape when stretched may be used. For instance, in still another embodiment, a plurality of discrete shapes may turn into a checkerboard-like design when stretched. In further embodiments, the stretchable panel may be configured to form words, symbols, or phrases when stretched.

The stretchable panel configured to change color can be made from various different constructions. For example, in one embodiment, the stretchable panel comprises a laminate having a gathered layer attached to a stretchable layer. The gathered layer may include peaks and valleys when the panel is in a relaxed state. In one embodiment, the gathered layer may be printed a certain color only at the peaks. Thus, when in a relaxed state, the color at the peaks predominates. As the panel is stretched, however, the gathered layer changes color as the color of the valleys of the gathered layer becomes exposed. In this embodiment, the gathered layer may change from a first color to a second color or may change from a first color to a second color and then to a third color.

In an alternative embodiment, the gathered layer may have a first color, while the stretchable layer may have a second color. In this embodiment, when the stretchable panel is in a substantially unstretched state, the color of the gathered layer predominates, which means that the color of the gathered layer has a dominating influence over the remaining layers. When the stretchable panel is stretched, however, the panel changes color due to the second color of the stretchable layer.

In another embodiment of the present invention, the stretchable panel comprises a polymer film or nonwoven, such as a polyolefin film or nonwoven, that changes color when stretched beyond a certain percentage. For instance, a polyethylene polymer may be used that has a density of from about 0.89 g/cc to about 0.95 g/cc and be configured to crystallize or craze when stretched a certain distance. In this manner, the polyethylene film changes color to indicate to the user of the absorbent article that the article either fits correctly or is approaching a size limit.

In still another embodiment, a polymer film may be contained in the stretchable panel that changes in reflectance as the film is stretched causing a visual color change. For example, in one embodiment, the polymer film may comprise a polarized film that increases in polarization as the film is stretched. The increase in polarization may result in a color change. The film may be made, for instance, from a polyurethane or a block copolymer that includes conjugated or aromatic groups incorporated into the polymer backbone. When stretched, an alignment occurs of the high electron density substituent groups which cause an increase in polarization and a change in light reflectance.

In one particular embodiment, the polarized film that increases in polarization when stretched may comprise a clear layer that is placed over a colored layer. When stretched, polarization of the top film layer may increase blocking out selected wavelengths of light. The increase in polarization then causes a color change to occur of the composite material. In particular, the polarizing layer acts as a color filter.

In constructing the stretchable panel so that the panel changes color as desired, it should also be understood that the above embodiments may be combined to arrive at further embodiments. For instance, polyethylene films and/or polarized films may be used in conjunction with a gathered layer that is printed at the peaks where the material has gathered. The different components may be combined to form the stretchable panel in a manner that produces either a two-color scheme or a three-color scheme as desired.

When forming a stretchable panel that undergoes a pattern change when stretched, various methods and techniques may be used to form the panel. For example, graphics may be printed on a film or on a nonwoven web that change in appearance when stretched. Alternatively, various graphics may be printed on multiple layers of a laminate that interact with each other when stretched to create a visual indicator.

The absorbent article made in accordance with the present invention may be, for instance, a diaper, a training pant, an incontinence product, a medical garment, a bandage, absorbent swimwear, a feminine hygiene product, and the like.

Other features and aspects of the present invention are discussed in greater detail below.

BRIEF DESCRIPTION OF THE DRAWINGS

A full and enabling disclosure of the present invention, including the best mode thereof to one skilled in the art, is set forth more particularly in the remainder of the specification, including reference to the accompanying figures, in which.

Figure 1:
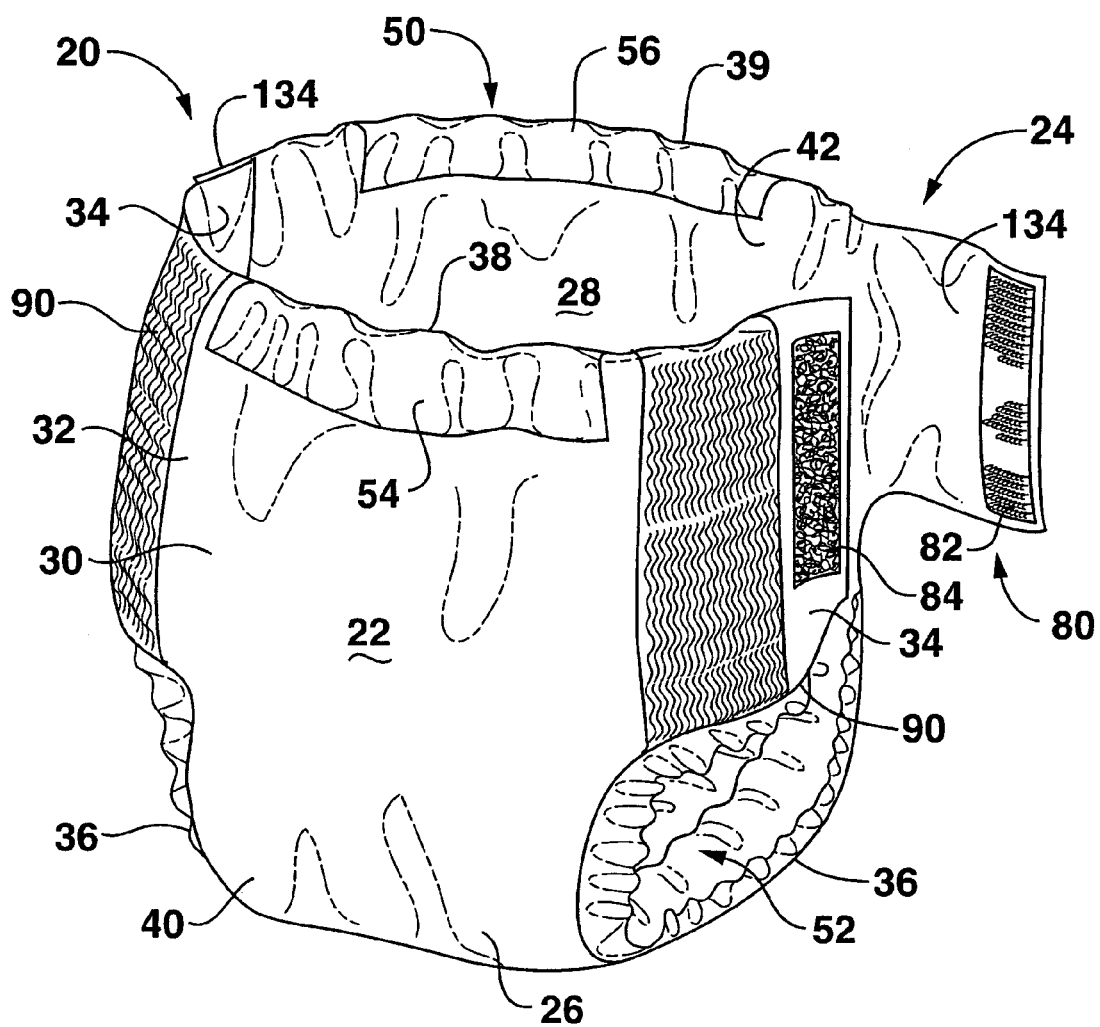
FIG. 1 is a perspective view of one embodiment of an absorbent article made in accordance with the present invention.

Repeat use of reference characters in the present specification and drawings is intended to represent the same or analogous features or elements of the present invention.

DEFINITIONS

As used herein, the "longitudinal direction" is a direction that extends from the front region of an absorbent article through a crotch region and to the back region.

As used herein, the "transverse direction" is the direction perpendicular to the longitudinal direction.

As used herein, the term "stretchable" refers to a material that may be stretchable and/or elastic (or elastomeric). That is, the material may be extended, deformed or the like, without breaking, and may or may not significantly retract after removal of an extending force.

As used herein, the term "extensible" refers to a material that is stretchable but is not elastic.

As used herein, the term "stretch bonded laminate" refers to a composite material having at least two layers in which one layer is a gatherable layer and the other layer is an elastic layer.

As used herein, the term "neck bonded laminate" refers to a composite material having an elastic member that is bonded to a non-extensible member while the non-elastomeric member is extended in the machine direction creating a necked material that is elastic in the cross-direction.

DETAILED DESCRIPTION

It is to be understood by one of ordinary skill in the art that the present discussion is a description of exemplary embodiments only, and is not intended as limiting the broader aspects of the present invention.

In general, the present invention is directed to an absorbent article that includes a visual fit indicator for indicating to the user whether the article is, for instance, too small or too large. The absorbent article may be, for instance, a diaper, a toilet training pant, an adult incontinence garment, a swim pant, a fitted brief, or the like. In one embodiment, the visual fit indicator comprises a stretchable panel that is incorporated into the absorbent article. The stretchable panel is constructed such that the panel changes in color or undergoes a pattern change in response to different levels of stress and strain applied to it. For example, in one embodiment, the stretchable panel may be configured to change color or pattern when the panel is stretched beyond a certain percentage indicating to the user that the article is approaching a size limit. In this embodiment, the stretchable panel changes from a first color to a second color.

In an alternative embodiment, the stretchable panel may be configured so that it is one color when the garment is too large (when not being stretched a significant amount), a second color when it fits the wearer and a third color when the article is too small.

As will be described in more detail below, the manner in which the stretchable panel changes color or pattern can vary depending upon the particular application. In one embodiment, for instance, the stretchable panel includes a top gathered layer that includes peaks and valleys when not being stretched. In accordance with the present invention, the peaks of the gathered layer may have a different color than the valley areas. Thus, when the stretchable panel is stretched, the gathered layer changes in color. In this embodiment, the valley areas of the gathered layer can be printed with multiple colors so that the gathered layer changes from a first color, to a second color and then to a third color as the stretchable panel is stretched.

In alternative embodiments, color change can occur by incorporating into the stretchable panel a film or nonwoven elastic material that changes color when stretched. For example, the film or elastic nonwoven can change color by changing reflectance, light scattering, or light transmission. Alternatively, the elastic film or nonwoven may undergo crystallization or may form microvoids when placed under stress causing a color change.

In one embodiment, multiple color changing materials may be incorporated into the stretchable panel in order to have a three-color change system.

In addition or instead of changing color, the stretchable panel of the present invention can also be configured to undergo a pattern change when stretched. For example, when stretched, the stretchable panel may form linear lines, rows or columns or may form a checkerboard-like pattern when stretched. In other embodiments, various graphics can be printed on the stretchable panel that undergo a change when stretched. In still other embodiments, a stretchable panel may be configured to form words, symbols, letters or phrases when stretched.

Figure 7:
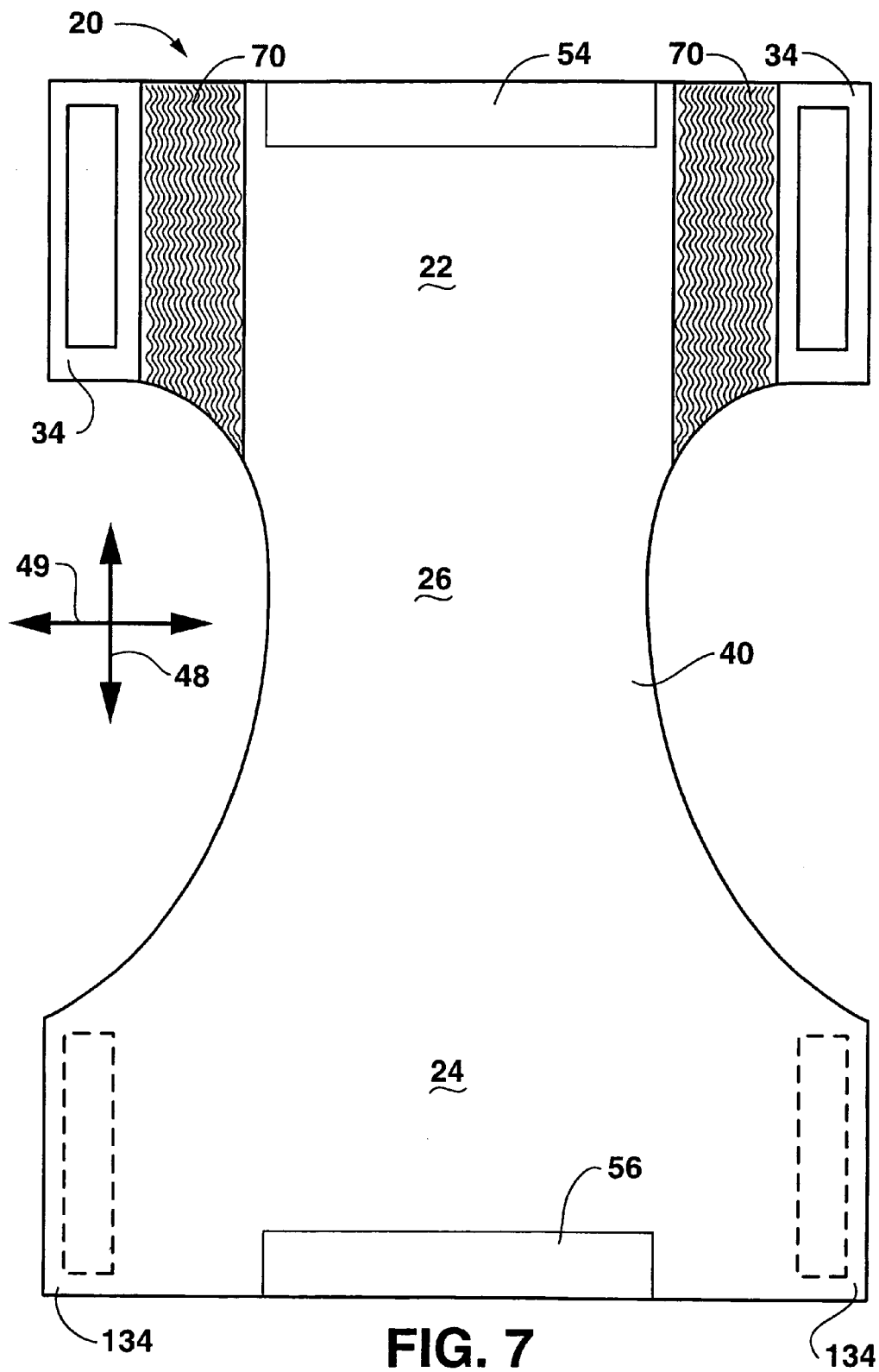
FIG. 7 is a plan view of the absorbent article illustrated in FIG. 1.
Figure 8:
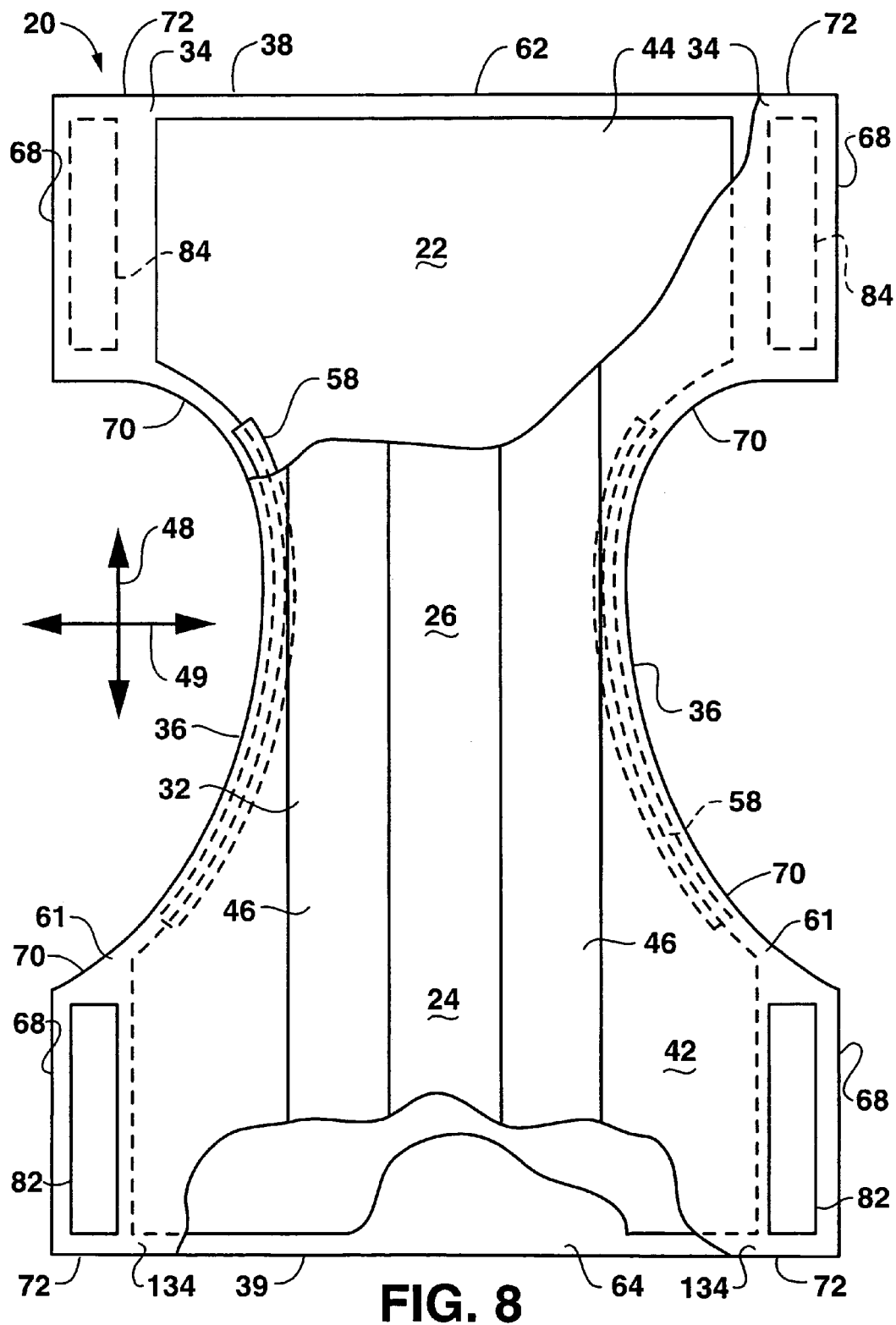
FIG. 8 is a plan view of the opposite side of the absorbent article illustrated in FIG. 7.

For exemplary purposes, a pair of training pants 20 is representatively illustrated in FIG. 1 in a partially fastened condition. The training pants 20 shown in FIG. 1 is also represented in FIGS. 7 and 8 in an opened and unfolded state. Specifically, FIG. 7 is a plan view illustrating the exterior side of the pants 20, while FIG. 8 illustrates the interior side of the pants 20. As shown in FIGS. 7 and 8, the pants 20 define a longitudinal direction 48 that extends from the front of the training pants when worn to the back of the training pants. Opposite to the longitudinal direction 48 is a lateral direction 49.

The pants 20 define a pair of longitudinal end regions, otherwise referred to herein as a front region 22 and a back region 24, and a center region, otherwise referred to herein as a crotch region 26, extending longitudinally between and interconnecting the front and back regions 22, 24. The pant 20 also defines an inner surface 28 adapted in use (e.g., positioned relative to the other components of the pants 20) to be disposed toward the wearer, and an outer surface 30 opposite the inner surface. The front and back regions 22, 24 are those portions of the pants 20, which when worn, wholly or partially cover or encircle the waist or mid-lower torso of the wearer. The crotch region 26 generally is that portion of the pants 20 which, when worn, is positioned between the legs of the wearer and covers the lower torso and crotch of the wearer. The training pants 20 have a pair of laterally opposite side edges 36 and a pair of longitudinally opposite waist edges, respectively designated front waist edge 38 and back waist edge 39.

The illustrated pants 20 may include a chassis 32, a pair of laterally opposite front side regions 34 extending laterally outward at the front region 22 and a pair of laterally opposite back side regions 134 extending laterally outward at the back region 24.

Referring to FIGS. 1, 7 and 8, the chassis 32 includes an outer cover 40 and a bodyside liner 42 (FIGS. 1 and 8) that may be joined to the outer cover 40 in a superimposed relation therewith by adhesives, ultrasonic bonds, thermal bonds or other conventional techniques. Referring to FIG. 8, the liner 42 may suitably be joined to the outer cover 40 along the perimeter of the chassis 32 to form a front waist seam 62 and a back waist seam 64. As shown in FIG. 8, the liner 42 may suitably be joined to the outer cover 40 to form a pair of side seams 61 in the front region 22 and the back region 24. The liner 42 can be generally adapted, i.e., positioned relative to the other components of the pants 20, to be disposed toward the wearer's skin during wear of the pants. The chassis 32 may further include an absorbent structure 44 particularly shown in FIG. 8 disposed between the outer cover 40 and the bodyside liner 42 for absorbing liquid body exudates exuded by the wearer, and may further include a pair of containment flaps 46 secured to the bodyside liner 42 for inhibiting the lateral flow of body exudates.

With the training pants 20 in the fastened position as partially illustrated in FIG. 1, the front and back side regions 34, 134 can be connected together by a fastening system 80 to define a three-dimensional pants configuration having a waist opening 50 and a pair of leg openings 52. The front and back side regions 34 and 134, upon wearing of the pants 20, thus include the portions of the training pants 20 which are positioned on the hips of the wearer. The waist edges 38 and 39 of the training pants 20 are configured to encircle the waist of the wearer and together define a waist opening 50 of the pants.

The elasticized containment flaps 46 as shown in FIG. 8 define a partially unattached edge which assumes an upright configuration in at least the crotch region 26 of the training pants 20 to form a seal against the wearer's body. The containment flaps 46 can extend longitudinally along the entire length of the chassis 32 or may extend only partially along the length of the chassis. Suitable constructions and arrangements for the containment flaps 46 are generally well known to those skilled in the art and are described in U.S. Pat. No. 4,704,116 issued Nov. 3, 1987 to Enloe, which is incorporated herein by reference.

To further enhance containment and/or absorption of body exudates, the training pants 20 may also suitably include a front waist elastic member 54 (FIG. 1), a rear waist elastic member 56, and leg elastic members 58 (FIG. 8), as are known to those skilled in the art. The waist elastic members 54 and 56 can be operatively joined to the outer cover 40 and/or the bodyside liner 42 and can extend over part or all of the waist edges 38, 39. The leg elastic members 58 can be operatively joined to the outer cover 40 and/or the bodyside liner 42 and positioned in the crotch region 26 of the training pants 20.

The waist elastic members 54 and 56, and the leg elastic members 58 can be formed of any suitable elastic material. As is well known to those skilled in the art, suitable elastic materials include sheets, strands or ribbons of natural rubber, synthetic rubber, or thermoplastic elastomeric polymers. The elastic materials can be stretched and adhered to a substrate, adhered to a gathered substrate, or adhered to a substrate and then elasticized or shrunk, for example with the application of heat, such that elastic retractive forces are imparted to the substrate. In one particular aspect, for example, the leg elastic members 58 may include a plurality of dry-spun coalesced multifilament spandex elastomeric threads sold under the trade name LYCRA and available from Invista, Wilmington, Del., U.S.A.

As shown in FIG. 8, the front and back side regions 34 and 134 each have a longitudinal outer edge 68, and a leg end edge 70 disposed toward the longitudinal center of the training pants 20, and waist end edges 72 disposed toward a longitudinal end of the training pants. The leg end edges 70 and the outer edges 68 of the side regions 34 and 134 form part of the pant side edges 36 of the training pants 20. The leg end edges 70 of the absorbent article 20 may be suitably curved and/or angled relative to the lateral direction 49 to provide a better fit around the wearer's legs. However, it is understood that only one of the leg end edges 70 may be curved or angled, such as the leg end edge of the back region 24, or alternatively, neither of the leg end edges may be curved or angled, without departing from the scope of the present invention. The waist end edges 72 are suitably parallel to the transverse axis 49. The waist end edges 72 of the front side regions 34 form part of the front waist edge 38 of the training pants 20, and the waist end edges 72 of the back side regions 134 form part of the back waist edge 39 of the pants. In the figures, the waist end edges 72 and the outer edges 68 are generally horizontal and vertical respectively. It should be understood, however, that in other embodiments, the waist end edges 72 and/or the outer edges 68 may have a curved, slanted or complex arrangement depending upon the particular application.

The side regions may be provided by a non-elastic material or an elastic material capable of stretching at least in a direction generally parallel to the lateral direction 49 of the training pants 20. Suitable elastic materials, as well as one process of incorporating elastic side regions into training pants, are described in the following U.S. Pat. No. 4,940,464 issued Jul. 10, 1990 to Van Gompel et al.; U.S. Pat. No. 5,224,405 issued Jul. 6, 1993 to Pohjola; U.S. Pat. No. 5,104,116 issued Apr. 14, 1992 to Pohjola; and U.S. Pat. No. 5,046,272 issued Sep. 10, 1991 to Vogt et al.; all of which are incorporated herein by reference. In particular aspects, the elastic material may include a stretch-thermal laminate (STL), a neck-bonded laminate (NBL), a reversibly necked laminate, or a stretch-bonded laminate (SBL) material. Methods of making such materials are well known to those skilled in the art and described in U.S. Pat. No. 4,663,220 issued May 5, 1987 to Wisneski et al.; U.S. Pat. No. 5,226,992 issued Jul. 13, 1993 to Morman; European Patent Application No. EP 0 217 032 published on Apr. 8, 1987 in the name of Taylor et al.; and PCT application WO 01/88245 in the name of Welch et al.; all of which are incorporated herein by reference to the extent that they are consistent (i.e., not in conflict) herewith. Alternatively, the side region material may include other woven or non-woven materials, such as those described later herein as being suitable for construction of the outer cover 40 and/or the bodyside liner 42; mechanically pre-strained composites; or stretchable but inelastic materials.

The fastening system 80 may include laterally opposite first fastening components 82 adapted for refastenable engagement to corresponding second fastening components 84. In one aspect, a front or outer surface of each of the fastening components 82, 84 includes a plurality of engaging elements. The engaging elements of the first fastening components 82 are adapted to repeatedly engage and disengage corresponding engaging elements of the second fastening components 84 to releasably secure the pants 20 in its three-dimensional configuration.

The fastening components 82, 84 may be any refastenable fasteners suitable for absorbent articles, such as adhesive fasteners, cohesive fasteners, mechanical fasteners, or the like. In particular aspects the fastening components include mechanical fastening elements for improved performance. Suitable mechanical fastening elements can be provided by interlocking geometric shaped materials, such as hooks, loops, bulbs, mushrooms, arrowheads, balls on stems, male and female mating components, buckles, snaps, or the like.

In the illustrated aspect, the first fastening components 82 include hook fasteners and the second fastening components 84 include complementary loop fasteners. Alternatively, the first fastening components 82 may include hook fasteners and the second fastening components 84 may be complementary loop fasteners. In another aspect, the fastening components 82, 84 can be interlocking similar surface fasteners, or adhesive and cohesive fastening elements such as an adhesive fastener and an adhesive-receptive landing zone or material; or the like. Although the training pants 20 illustrated in FIG. 1 indicate the back side regions 134 overlapping the front side regions 34 upon connection thereto, which is convenient, the training pants 20 can also be configured so that the front side regions 34 overlap the back side regions 134 when connected. One skilled in the art will recognize that the shape, density and polymer composition of the hooks and loops may be selected to obtain the desired level of engagement between the fastening components 82, 84. Optionally, either one or both of the fastening components 82, 84 may be provided by one of the inner or outer surfaces 28 and 30 of the side regions 34 and 134. Suitable fastening systems are also disclosed in the previously incorporated PCT Patent Application WO 00/37009 published Jun. 29, 2000 by A. Fletcher et al. and the previously incorporated U.S. Pat. No. 6,645,190 issued Nov. 11, 2003 to Olson et al.

In addition to the components described above, the absorbent article 20 may further include a surge management layer which may be optionally located adjacent the liner 42 and/or the absorbent structure 44 and attached to various components in the article 20 such as the absorbent structure 44 or the bodyside liner 42 by methods known in the art, such as by using an adhesive. A surge management layer helps to decelerate and diffuse surges or gushes of liquid that may be rapidly introduced into the absorbent structure of the article. Desirably, the surge management layer can rapidly accept and temporarily hold the liquid prior to releasing the liquid into the storage or retention portions of the absorbent structure. Examples of suitable surge management layers are described in U.S. Pat. No. 5,486,166; and U.S. Pat. No. 5,490,846. Other suitable surge management materials are described in U.S. Pat. No. 5,820,973. The entire disclosures of these patents are hereby incorporated by reference herein to the extent they are consistent (i.e., not in conflict) herewith.

In the embodiment shown in FIG. 1, the side regions 34 and 134 of the absorbent article 20 are releasably attachable. It should be understood, however, that in other embodiments, the side regions 34 and 134 may be permanently joined together or may be integral with the chassis 32. For instance, referring to FIG. 2, a perspective view of an alternative embodiment of an absorbent article generally 20 made in accordance with the present invention is shown. Similar reference numerals have been used to indicate similar elements. As shown, in this embodiment, the side regions are integral with the remainder of the article. Alternatively, however, a seam may be present where the sides of the article have been bonded together. The side regions may be bonded together using, for instance, ultrasonic bonding, thermal bonding or an adhesive. In this embodiment, the absorbent article is pulled over the legs when being worn.

Figure 2:
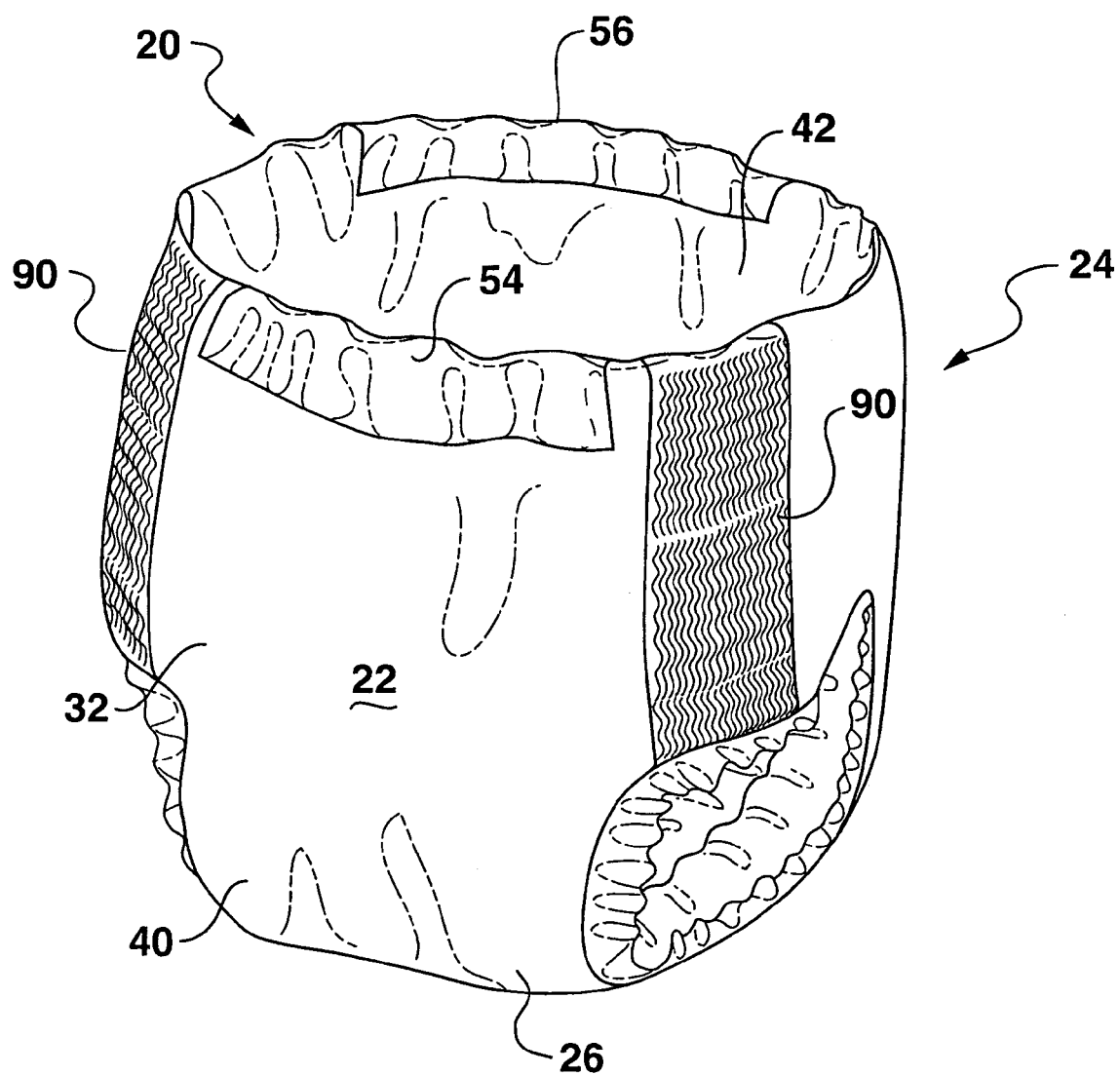
FIG. 2 is a perspective view of an alternative embodiment of an absorbent article made in accordance with the present invention.

As shown in FIGS. 1 and 2, each of the absorbent articles 20 further include a pair of stretchable panels 90 that, in accordance with the present invention, are configured to change color and/or undergo a pattern change as the panels are stretched. The stretchable panels 90 are provided on the article to act as a visual fit indicator. The stretchable panels, for instance, may indicate when the article is too small, may indicate when the article is the proper size, and/or may indicate when the article is too large for a particular wearer. The stretchable panel may, for instance, change from a first color to a second color when stretched. Alternatively, the stretchable panel may be configured to change from a first color, to a second color and then to a third color as the panel is stretched beyond certain limits.

Figure 5A:
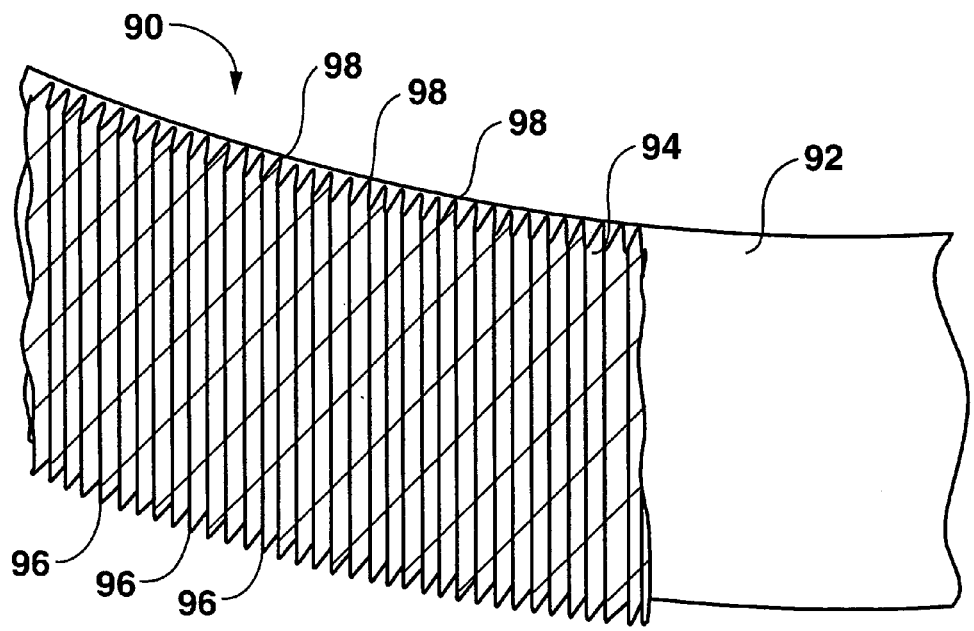
FIGS. 5A and 5B are perspective views with cutaway portions of a stretchable panel made in accordance with the present invention.
Figure 5B:
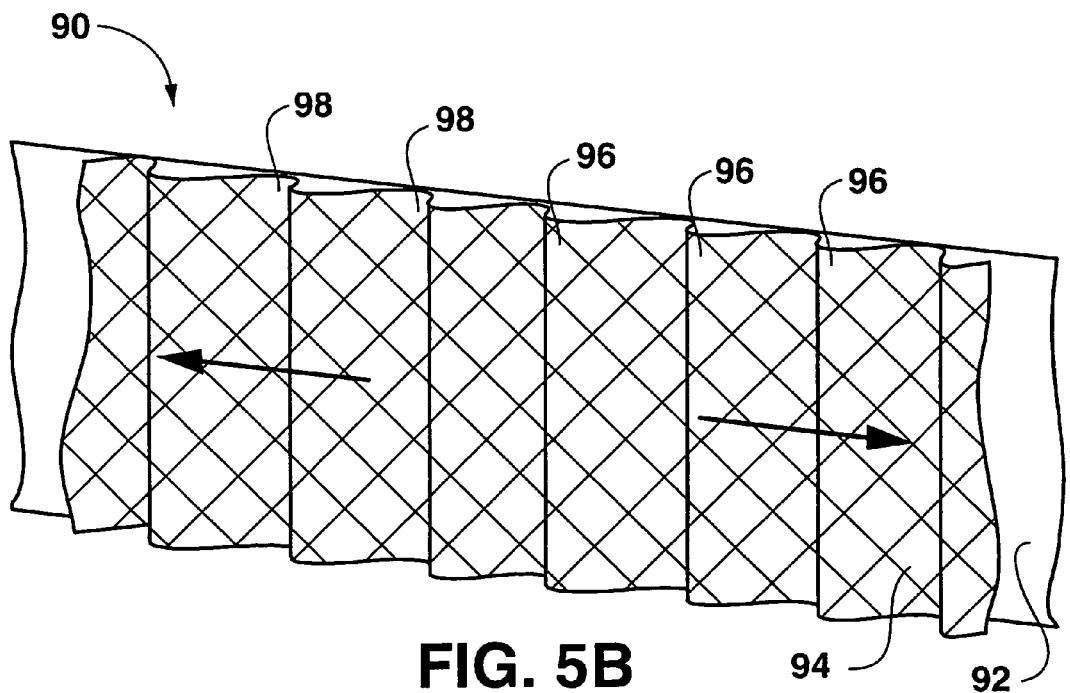

In general, the stretchable panel 90 can be made from any single or multi-layered material that is capable of changing in visual appearance, such as in color or pattern, when subjected to stress and/or strain. Referring to FIGS. 5A and 5B, for instance, one particular embodiment of a stretchable panel 90 that may be used in accordance with the present invention is illustrated.

In the embodiment shown in FIGS. 5A and 5B, the stretchable panel 90 includes a stretchable layer 92 that may be, for instance, an elastic film or an elastic nonwoven. The stretchable layer 92, which may also be elastic, is laminated to a gathered layer 94. The gathered layer 94 may be, for instance, a grooved material, a film, a nonwoven material, a woven material, or a knitted material. In one embodiment, the stretchable panel 90 as shown in FIG. 5A may be a stretch bonded laminate, a neck bonded laminate, or the like.

In FIG. 5A, the stretchable panel 90 is shown in an unstretched state. In this state, the gathered layer 94 includes peaks 96 and valleys 98. In one embodiment, in order to construct the stretchable panel 90 so as to change color when stretched, the peak areas 96 may be a different color than the valley areas 98. For example, the gathered layer 94 may be printed a first color only at the peak areas 96 and printed a second color within the valley areas 98. Printing may be done using, for instance, any suitable printing device such as an inkjet printer or a flexigraphic printer.

By having the peaks 96 and the valleys 98 a different color, the stretchable panel 90 will change color when elongated from a relaxed state to a stretched state. For example, when in a relaxed state, the color of the peaks 96 predominate. As the material is elongated or stretched, however, the color of the valleys eventually dominate causing the color or visual appearance of the panel 90 to change. For example, FIG. 5B demonstrates the stretchable panel 90 being stretched allowing the valley areas 98 to become visible.

In the embodiment described above, the color change that occurs as the stretchable panel 90 is stretched may be used to indicate either that the absorbent article is reaching a size limit or alternatively that the absorbent article fits correctly.

As stated above, in addition to color changes, the stretchable panel 90 may also be configured to undergo a pattern change when stretched. For example, in one embodiment, a graphic may be printed only on the peaks 96 of the gathered layer 94 as shown in FIG. 5A. The valleys 98, on the other hand, may also be printed with a complimentary graphic or with a particular color. When stretched, the graphic of the peaks 96 may merge with the graphic of the valleys 98 to create a visual indicator to the user. The graphic may be, for instance, any particular shapes, designs, cartoon characters, symbols, words, phrases, and the like.

In one embodiment, the stretchable panel as shown in FIGS. 5A and 5B may also be configured to display a three-color scheme as the panel is stretched. For example, in one hypothetical embodiment, the gathered layer may initially have a red color. The peaks 96 can then be printed a different color, such as a blue color. When the stretchable panel is in a substantially relaxed state, the panel appears blue due to the color of the peaks. As the panel is stretched into an optimal fit zone, however, the underlying red color of the valley areas start to show through, which makes the panel appear to be purple as more red is exposed and mingles with the blue. Once stretched beyond the optimal fit zone, however, the red color of the valley areas begins to dominate making the panel appear red, which indicates that the size is too small.

Of particular advantage, the stretchable panel as described above may be constructed so that the color or pattern changes occur as desired. For example, depending upon the construction of the stretchable panel, where the stretchable panel is located, the particular absorbent article that is being combined with the stretchable panel are all factors to consider when determining exactly when a color change may occur as the material is stretched. In one embodiment, for instance, the stretchable panel remains a first color when being stretched from zero to about 15%. Percent stretch as used herein refers to the amount the panel is stretched based on its original unstretched length. For example, a panel that is stretched 100% is stretched until its length doubles in size.

In one embodiment, once the stretchable panel is stretched beyond 15%, it may be desirable for the panel to change from a first color to a second color. In a three-color scheme, the second color is an indication that the article properly fits on the wearer. Once stretched beyond about 35%, in one embodiment, the article may change to a third color indicating that the article is too small for the wearer. It should be understood, however, that the above ranges are merely exemplary and can vary dramatically depending upon the desired results.

It should be understood that the above percentages merely represent one embodiment of the present invention. In alternative embodiments, for instance, a color or pattern change may not be desired until the panel is stretched over 50%. Still, in other embodiments, it may be desired for the stretchable panel to change color or to undergo a pattern change when stretched only 5%. For instance, if the panel is aligned in the longitudinal direction as opposed to the lateral direction, less stretch prior to a color or pattern change may be needed.

Figure 6A:
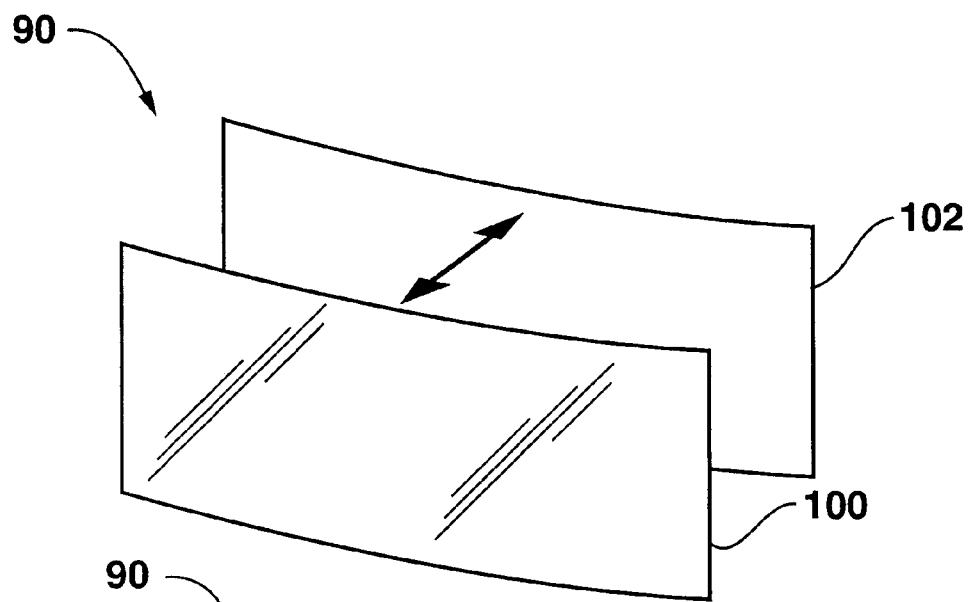
FIGS. 6A, 6B and 6C are perspective views of an alternative embodiment of a stretchable panel made in accordance with the present invention.
Figure 6B:
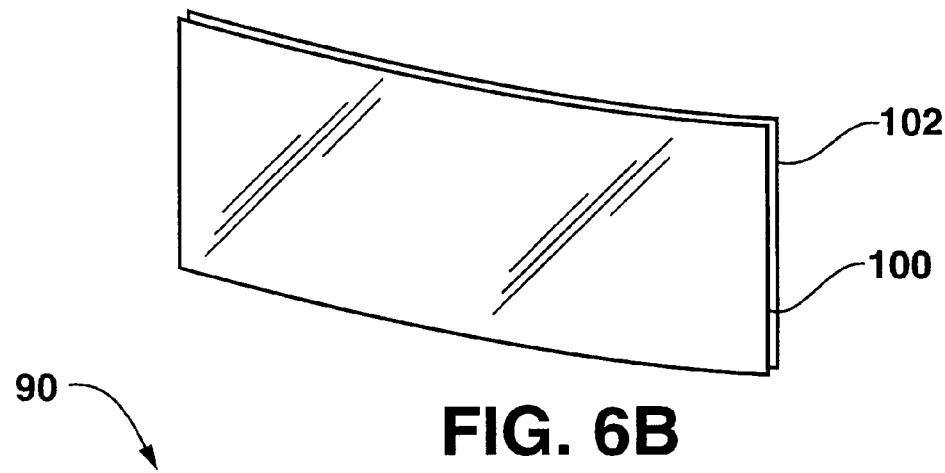
Figure 6C:
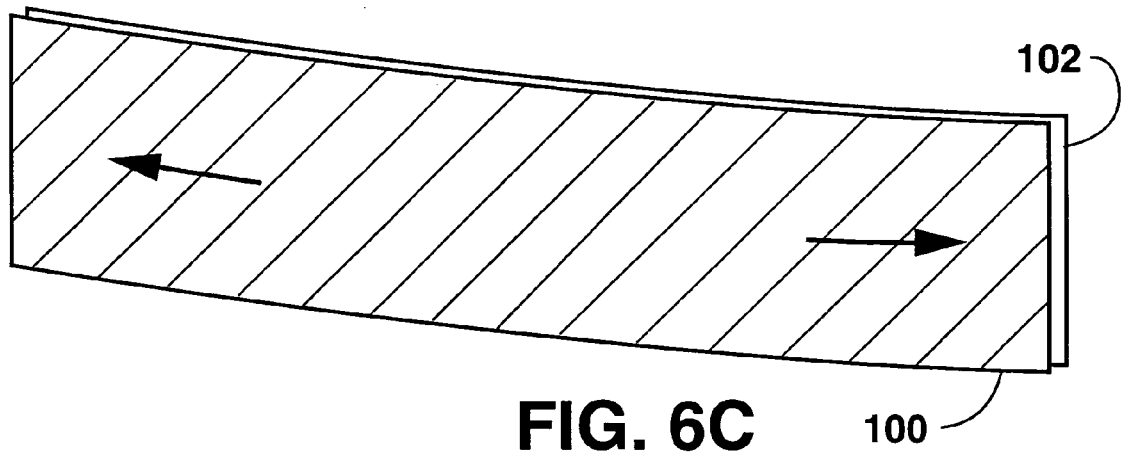

Referring to FIGS. 6A, 6B and 6C, an alternative embodiment of a stretchable panel 90 made in accordance with the present invention is shown. In this embodiment, as shown in FIG. 6A, the stretchable panel 90 includes a stretchable layer 100 optionally laminated to an elastic layer 102. Elastic layer 102 may be used if the stretchable panel 90 is intended to be stretchable and elastic as opposed to being only extensible. Stretchable layer 100 and elastic layer 102 may be films, nonwoven materials, woven materials, knitted materials, or mixtures thereof.

Stretchable layer 100, however, is a material that is capable of changing color when stretched. For example, in one embodiment, the stretchable layer 100 comprises a polymer film that changes its light scattering and/or reflectance properties when stretched. For example, stretchable layer 100 in one particular embodiment comprises a polyolefin, such as a polyethylene film that crystallizes or crazes when subjected to stress and strain which results in a color change. The polyethylene film, for instance, may have an initial color, such as green or blue. When stretched, however, the polyethylene crystallizes or crazes turning white as illustrated in FIG. 6C.

In this embodiment, the polymer film or nonwoven 100 can be made from any suitable polymer such as a polypropylene or a polyethylene that is capable of crystallizing as described above. In one embodiment, for instance, a polyethylene is used that has a density of from about 0.89 g/cc to about 0.95 g/cc, such as from about 0.9 g/cc to about 0.94 g/cc. In one embodiment, the stretchable panel 90 as shown in FIGS. 6A-6C may be incorporated into an absorbent article and, when the panel changes color, may be used to indicate that the article is too small for the wearer.

In an alternative embodiment of the present invention, the polymer film or nonwoven 100 may be printed with a graphic that undergoes a pattern change when stretched. For example, in one embodiment, discrete shapes such as blocks are printed onto the film. As the film is stretched, the discrete shapes or blocks form linear lines that may then be used to indicate whether or not the article fits properly. In other embodiments, various other graphics may be printed onto the film that cause other pattern changes to occur. For instance, in other embodiments, a checkerboard-like pattern may form when the film is stretched. In still other embodiments, words, phrases or symbols may form as the film is stretched. Various designs, such as characters, may also be printed on the film that change in some manner as the film is stretched.

In another alternative embodiment of the present invention, stretchable layer 100 and/or the elastic layer 102 may comprise a film that polarizes light or increases in polarization when stretched. For example, polarized films typically contain long-chain molecules that are aligned within the film in the same direction. When the long-chain molecules are stretched, the ability of the film to polarize light increases.

In this embodiment, any suitable film that is capable of increasing in polarization when stretched may be used. The film may be stretchable or the film may be elastic. The film, for instance, may be made from polyurethane, a block copolymer, or a polyamide. The block copolymer may be, for instance, a styrene-ethylene butylene-styrene block copolymer (S-EB-S), a styrene-isoprene-styrene block copolymer (S-I-S), and the like.

In order to make the above polymeric materials capable of polarizing light, the polymer backbones are reacted with a substituent group, such as a conjugated or aromatic substituent group. The substituent group, for instance, may be a halide or an aromatic. As described above, polarization of the film increases as the film is stretched due to the alignment of the polymer chains contained within the film. An increase in polarization of the film may cause the film to change color.

Alternatively, the polarized film may be combined with a second layer and an increase in polarization of the film may cause the second layer to change color. For example, in one embodiment, layer 102 as shown in FIG. 6A may comprise a colored layer, while layer 100 may comprise a clear polarized layer. When the stretchable panel 90 is stretched, polarization of the top layer 100 increases blocking out selected wavelengths of light. As a result, the appearance of the bottom layer 102 may change. Basically, the polarizing layer 100 acts as a color filter. For example, if layer 102 were green and the polarizing layer 100 was configured to polarize/filter blue light when stretched, the panel 90 would turn yellow when stretched.

In one particular embodiment of the present invention, the second layer may be printed with a graphic, such as a design. As the polarized layer is stretched, the underlying graphic may change color.

In still other embodiments of the present invention, the stretchable panel as shown in FIGS. 6A-6C may include a gathered layer 94 as shown in FIGS. 5A and 5B. The gathered layer, for instance, may be made from a low basis weight nonwoven, such as a spunbond or a meltblown web that is at least partially transparent for allowing the stretchable panel 90 as shown in FIGS. 6A, 6B and 6C from being visible. In this embodiment, for instance, the peaks of the gathered layer may be printed a first color that predominates when the panel is in a relaxed condition. As the panel is stretched, however, the peak areas of the gathered layer take up more visible surface area exposing the underlying material. As the panel is further stretched, the underlying material may change color as described above for creating a panel that undergoes two color changes as the panel is stretched.

In the embodiments shown in FIGS. 1 and 2, the absorbent article 20 includes a pair of opposing stretchable panels 90 located on the sides of the garment towards the front. It should be understood, however, that the absorbent article may include more or fewer stretchable panels 90. Further, the location and shape of the stretchable panel 90 may change depending upon the particular application. For example, referring to FIG. 3, an alternative embodiment of an absorbent article 120 made in accordance with the present invention is shown. In this embodiment, the absorbent article 120 includes a single stretchable panel 190 located generally in the front region. More particularly, in this embodiment, the stretchable panel 190 comprises an elastic strip in the front region that generally circumscribes the hip circumference of a user.

Figure 3:
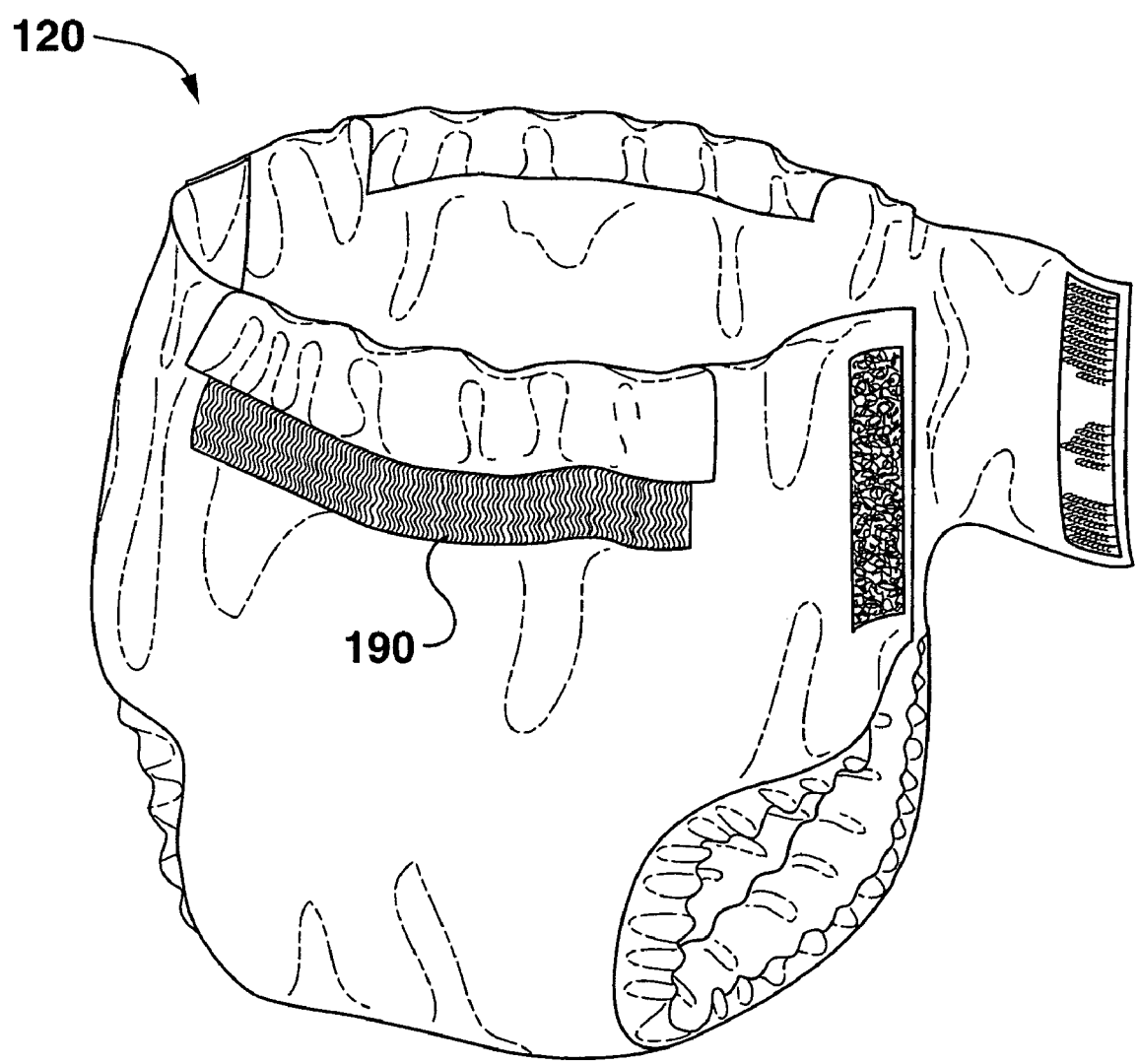
FIG. 3 is a perspective view of still another embodiment of an absorbent article made in accordance with the present invention.

In the embodiment shown in FIGS. 1, 2 and 3, the stretchable panel 90 is generally configured to stretch in the transverse direction. In an alternative embodiment, however, it should be understood that the stretchable panel may also be configured to stretch in the longitudinal direction. In this embodiment, for instance, the stretchable panel may be used as a visual indicator to indicate whether or not the rise of the article is correct and fits properly on the user. In still other embodiments, the stretchable panel may be configured to stretch not only in the longitudinal direction but also in the transverse direction.

Figure 4:
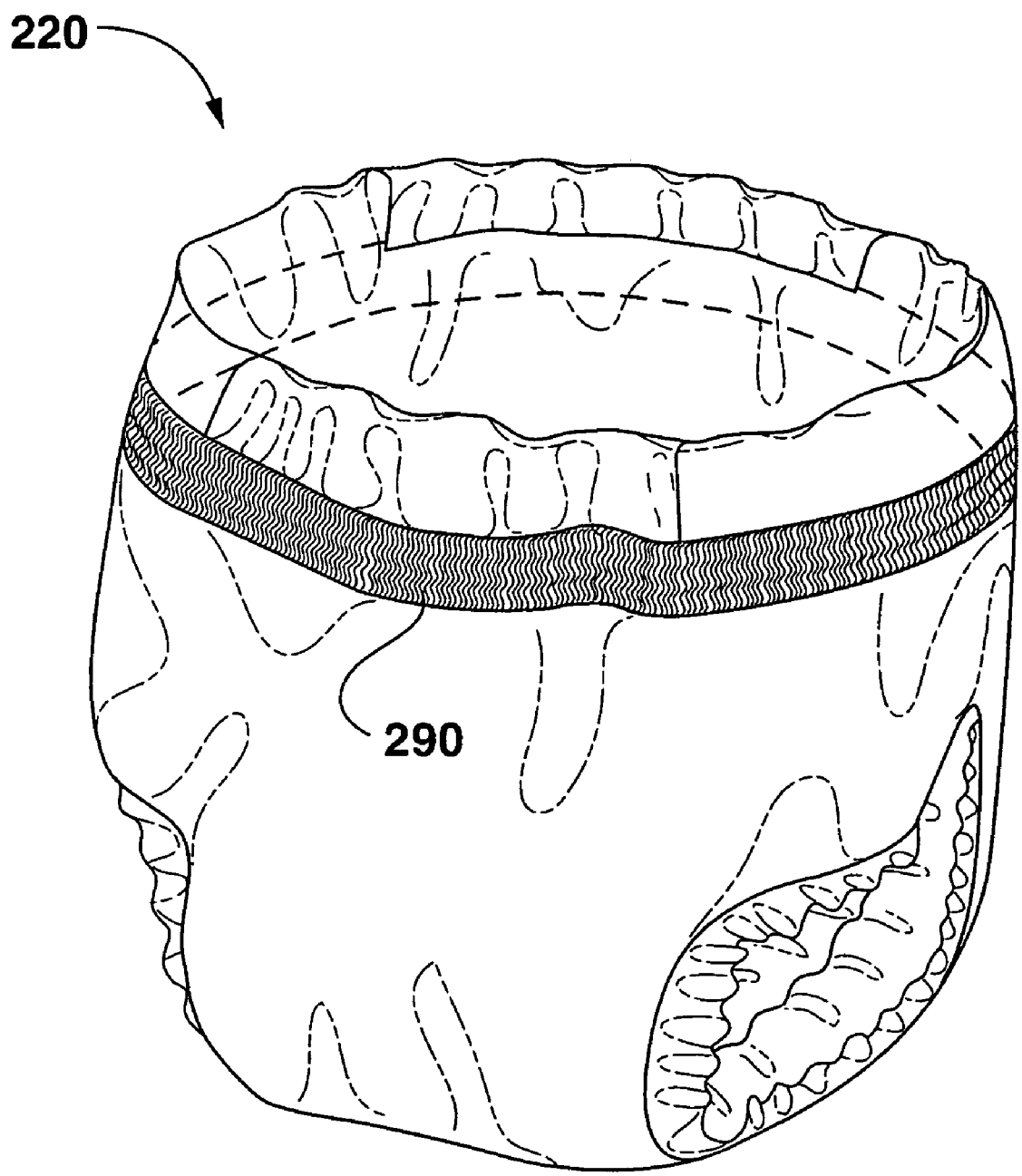
FIG. 4 is a perspective view of still another embodiment of an absorbent article that may be made in accordance with the present invention.

Still another embodiment of an absorbent article 220 made in accordance with the present invention is shown in FIG. 4. As illustrated, the absorbent article 220 includes a color changing size indicator panel 290. In this embodiment, the panel 290 comprises a band that extends around the entire circumference of the article. The band is located generally at the hip circumference of the user where the article is typically subjected to the most stress and strain.

In still other embodiments, the color changing size indicator of the present invention may comprise a single color changing thread that is positioned around the circumference of the article at the hips.

Figure 9:
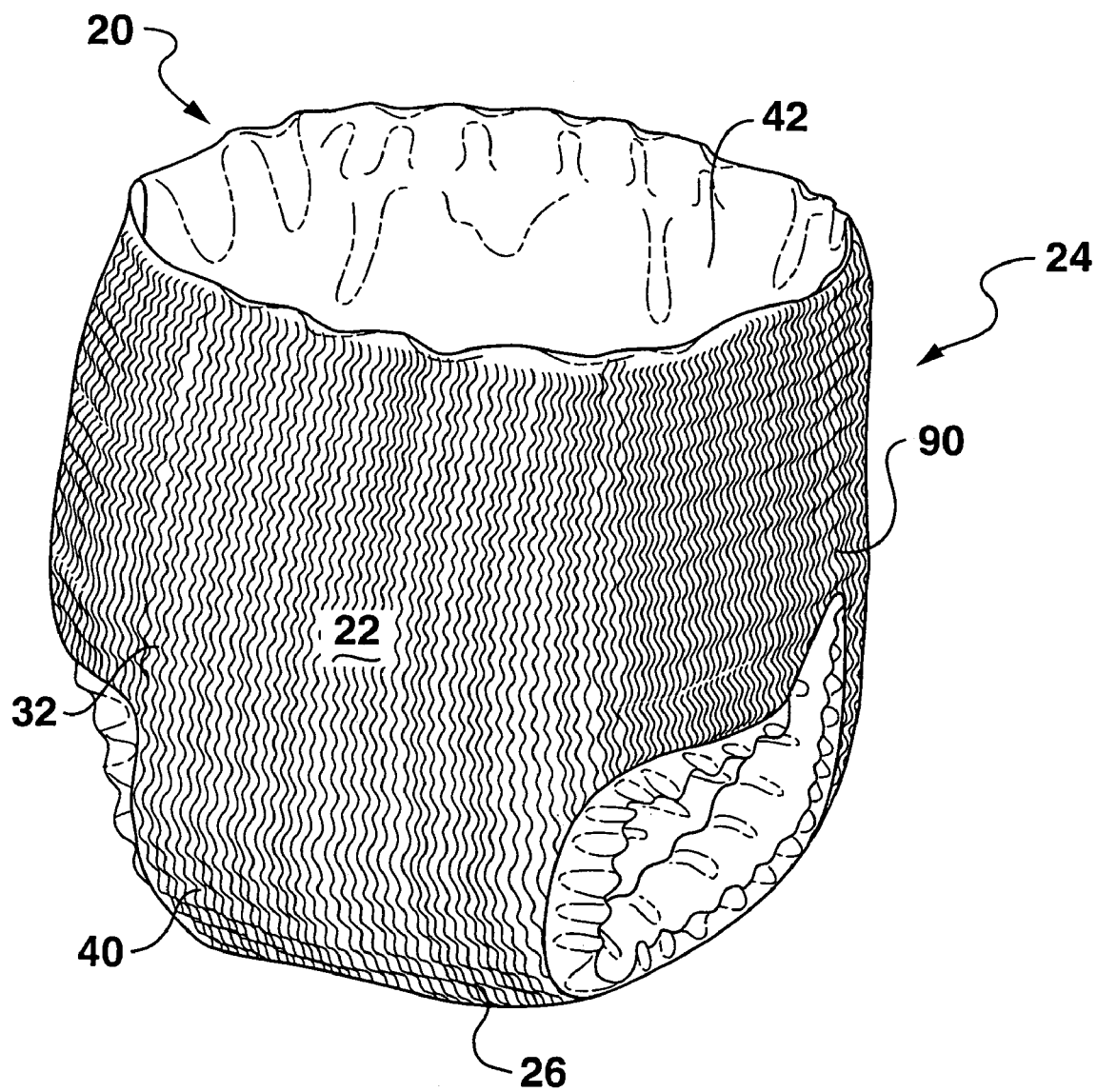
FIG. 9 is a perspective view of another embodiment of an absorbent article made in accordance with the present invention.

Referring to FIG. 9, another embodiment of an absorbent article generally 20 made in accordance with the present invention is shown. As illustrated, the absorbent article 20 includes a chassis 32 comprising a front region 22, a back region 24, and a crotch region 26. In this embodiment, the entire chassis 32 is formed from the stretchable panel 90. In this embodiment, the stretchable panel may be configured to change color or undergo a pattern change at any point in the garment should the garment be overstretched at that area. The stretchable panel 90 may be constructed according to any of the embodiments described above.

As described above with reference particularly to FIGS. 1, 7 and 8, the absorbent article 20 includes an outer cover 40, a bodyside liner 42, and an absorbent structure 44. These elements of the absorbent article may be made from conventional materials or can be made from the stretchable panel itself as shown in FIG. 9.

The outer cover 40 may be made from a material that is substantially liquid and permeable, and can be elastic, stretchable or nonstretchable. The outer cover 40 can be a single layer of liquid and permeable material, or may include a multi-layered laminate structure in which at least one of the layers is liquid and permeable. For instance, the outer cover 40 can include a liquid permeable outer layer and a liquid and permeable inner layer that are suitably joined together by a laminate adhesive.

For example, in one embodiment, the liquid permeable outer layer may be a spunbond polypropylene nonwoven web. The spunbond web may have, for instance, a basis weight of from about 15 gsm to about 25 gsm.

The inner layer, on the other hand, can be both liquid and vapor impermeable, or can be liquid impermeable and vapor permeable. The inner layer is suitably manufactured from a thin plastic film, although other flexible liquid impermeable materials may also be used. The inner layer prevents waste material from wetting articles such as bedsheets and clothing, as well as the wearer and caregiver. A suitable liquid impermeable film may be a polyethylene film having a thickness of about 0.2 mm.

A suitable breathable material that may be used as the inner layer is a microporous polymer film or a nonwoven fabric that has been coated or otherwise treated to impart a desired level of liquid impermeability. Other "non-breathable" elastic films that may be used as the inner layer include films made from block copolymers, such as styrene-ethylene-butylene-styrene or styrene-isoprene-styrene block copolymers.

As described above, the absorbent structure is positioned in between the outer cover and a liquid permeable bodyside liner 42. The bodyside liner 42 is suitably compliant, soft feeling, and non-irritating to the wearer's skin. The bodyside liner 42 can be manufactured from a wide variety of web materials, such as synthetic fibers, natural fibers, a combination of natural and synthetic fibers, porous foams, reticulated foams, apertured plastic films, or the like. Various woven and nonwoven fabrics can be used for the bodyside liner 42. For example, the bodyside liner can be made from a meltblown or spunbonded web of polyolefin fibers. The bodyside liner can also be a bonded-carded web composed of natural and/or synthetic fibers.

The bodyside liner 42 may be constructed to be extensible but not elastic. In other embodiments, however, the liner 42 may be configured to be elastic in the longitudinal direction, in the transverse direction, or in both directions.

A suitable liquid permeable bodyside liner 42 is a nonwoven bicomponent web having a basis weight of about 27 gsm. The nonwoven bicomponent can be a spunbond bicomponent web, or a bonded carded bicomponent web. Suitable bicomponent staple fibers include a polyethylene/polypropylene bicomponent fiber. In this particular embodiment, the polypropylene forms the core and the polyethylene forms the sheath of the fiber. Other fiber orientations, however, are possible.

The material used to form the absorbent structure 44, for example, may include cellulosic fibers (e.g., wood pulp fibers), other natural fibers, synthetic fibers, woven or nonwoven sheets, scrim netting or other stabilizing structures, superabsorbent material, binder materials, surfactants, selected hydrophobic materials, pigments, lotions, odor control agents or the like, as well as combinations thereof. In a particular embodiment, the absorbent web material is a matrix of cellulosic fluff and superabsorbent hydrogel-forming particles. The cellulosic fluff may comprise a blend of wood pulp fluff. One preferred type of fluff is identified with the trade designation CR 1654, available from US Alliance Pulp Mills of Coosa, Ala., USA, and is a bleached, highly absorbent wood pulp containing primarily soft wood fibers. As a general rule, the superabsorbent material is present in the absorbent web in an amount of from about 0 to about 90 weight percent based on total weight of the web. The web may have a density within the range of about 0.1 to about 0.45 grams per cubic centimeter.

Superabsorbent materials are well known in the art and can be selected from natural, synthetic, and modified natural polymers and materials. The superabsorbent materials can be inorganic materials, such as silica gels, or organic compounds, such as crosslinked polymers. Typically, a suberabsorbent material is capable of absorbing at least about 15 times its weight in liquid, and suitably is capable of absorbing more than about 25 times its weight in liquid. Suitable superabsorbent materials are readily available from various suppliers. For example, FAVOR SXM 880 superabsorbent is available from Stockhausen, Inc., of Greensboro, N.C., USA; and Drytech 2035 is available from Dow Chemical Company, of Midland, Mich., USA.

In addition to cellulosic fibers and superabsorbent materials, the absorbent pad structures may also contain adhesive elements and/or synthetic fibers that provide stabilization and attachment when appropriately activated. Additives such as adhesives may be of the same or different aspect from the cellulosic fibers; for example, such additives may be fibrous, particulate, or in liquid form; adhesives may possess either a curable or a heat-set property. Such additives can enhance the integrity of the bulk absorbent structure, and alternatively or additionally may provide adherence between facing layers of the folded structure.

The absorbent materials may be formed into a web structure by employing various conventional methods and techniques. For example, the absorbent web may be formed with a dry-forming technique, an airlaying technique, a carding technique, a meltblown or spunbond technique, a wet-forming technique, a foam-forming technique, or the like, as well as combinations thereof. Layered and/or laminated structures may also be suitable. Methods and apparatus for carrying out such techniques are well known in the art.

The absorbent web material may also be a coform material. The term "coform material" generally refers to composite materials comprising a mixture or stabilized matrix of thermoplastic fibers and a second non-thermoplastic material. As an example, coform materials may be made by a process in which at least one meltblown die head is arranged near a chute through which other materials are added to the web while it is forming. Such other materials may include, but are not limited to, fibrous organic materials such as woody or non-woody pulp such as cotton, rayon, recycled paper, pulp fluff and also superabsorbent particles or fibers, inorganic absorbent materials, treated polymeric staple fibers and the like. Any of a variety of synthetic polymers may be utilized as the melt-spun component of the coform material. For instance, in some embodiments, thermoplastic polymers can be utilized. Some examples of suitable thermoplastics that can be utilized include polyolefins, such as polyethylene, polypropylene, polybutylene and the like; polyamides; and polyesters. In one embodiment, the thermoplastic polymer is polypropylene. Some examples of such coform materials are disclosed in U.S. Pat. No. 4,100,324 to Anderson, et al.; U.S. Pat. No. 5,284,703 to Everhart, et al.; and U.S. Pat. No. 5,350,624 to Georger, et al.; which are incorporated herein in their entirety by reference for all purposes.

It is also contemplated that elastomeric absorbent web structures may be used. For example, an elastomeric coform absorbent structure may be used to form the absorbent structure according to the invention. Examples of such elastomeric coform materials are provided in U.S. Pat. No. 5,645,542, incorporated herein in its entirety for all purposes. As another example, a suitable absorbent elastic nonwoven material may include a matrix of thermoplastic elastomeric nonwoven filaments with the matrix including a plurality of absorbent fibers and a super-absorbent material. U.S. Pat. No. 6,362,389 describes such a nonwoven material and is incorporated herein by reference in its entirety for all purposes. Absorbent elastic nonwoven materials are useful in a wide variety of personal care articles where softness and conformability, as well as absorbency and elasticity, are important.

The absorbent web may also be a nonwoven web comprising synthetic fibers. The web may include additional natural fibers and/or superabsorbent material. The web may have a density in the range of about 0.1 to about 0.45 grams per cubic centimeter. The absorbent web can alternatively be a foam.

These and other modifications and variations to the present invention may be practiced by those of ordinary skill in the art, without departing from the spirit and scope of the present invention, which is more particularly set forth in the appended claims. In addition, it should be understood that aspects of the various embodiments may be interchanged both in whole or in part. Furthermore, those of ordinary skill in the art will appreciate that the foregoing description is by way of example only, and is not intended to limit the invention so further described in such appended claims.

What is claimed:

1. An absorbent article comprising:
a chassis defining a waist opening opposite two leg openings, the chassis comprising an outer cover, a bodyside liner, and an absorbent structure positioned in between the outer cover and the bodyside liner;
at least one stretchable and elastic panel associated with the chassis, the stretchable panel being positioned to stretch when the absorbent article is placed on a wearer, the stretchable panel changing color or undergoing a pattern change when the panel is stretched beyond a certain percentage indicating to the user that the article is approaching a size limit, the stretchable panel comprising a laminate having a gathered layer attached to a stretchable layer, wherein the gathered layer has a first color and the stretchable layer has a second color and wherein when the stretchable panel is in a substantially unstretched state, the color of the gathered layer predominates and wherein, when the stretchable panel is stretched, the panel changes color due to the second color of the stretchable layer.

2. An absorbent article as defined in claim 1, wherein the stretchable layer comprises a polyolefin film that changes color when stretched beyond a certain percentage.

3. An absorbent article as defined in claim 1, wherein the stretchable panel exhibits a first color when in a substantially unstretched state, exhibits a second color when stretched within a first percentage range, and exhibits a third color when stretched within a second percentage range, the second percentage range being greater than the first percentage range.

4. An absorbent article as defined in claim 1, wherein the stretchable panel comprises a side region of the chassis.

5. An absorbent article as defined in claim 1, wherein the stretchable panel comprises a waist panel of the chassis.

6. An absorbent article as defined in claim 1, wherein the stretchable panel is elastic.

7. An absorbent article as defined in claim 1, wherein the stretchable layer comprises a polyolefin layer.

8. An absorbent article as defined in claim 7, wherein the stretchable layer comprises a polyethylene or polypropylene layer.

9. An absorbent article as defined in claim 3, wherein the stretchable layer comprises a polyolefin layer, wherein the polyolefin layer changes from the second color to the third color when the layer is stretched beyond a certain percentage.

10. An absorbent article as defined in claim 1, wherein the chassis defines a hip circumference and wherein the stretchable panel extends around the hip circumference.

11. An absorbent article as defined in claim 1, wherein the article comprises a diaper.

12. An absorbent article comprising:
a chassis defining a waist opening opposite two leg openings, the chassis comprising an outer cover, a bodyside liner, and an absorbent structure positioned in between the outer cover and the bodyside liner;
at least one stretchable and elastic panel associated with the chassis, the stretchable panel being positioned to stretch when the absorbent article is placed on a wearer, the stretchable panel changing color or undergoing a pattern change when the panel is stretched beyond a certain percentage indicating to the user that the article is approaching a size limit, the stretchable panel comprising a laminate having a gathered layer attached to a stretchable layer, wherein the gathered layer includes peaks and valleys when the stretchable panel is in a relaxed state and wherein the gathered layer is printed a certain color only at the peaks.

13. An absorbent article as defined in claim 12, wherein the stretchable panel comprises a side region of the chassis.

14. An absorbent article as defined in claim 12, wherein the stretchable panel comprises a waist panel of the chassis.

15. An absorbent article as defined in claim 12, wherein the stretchable panel is elastic.

16. An absorbent article as defined in claim 12, wherein the stretchable layer comprises a polyolefin layer.

17. An absorbent article as defined in claim 16, wherein the stretchable layer comprises a polyethylene or polypropylene layer.

18. An absorbent article as defined in claim 12, wherein the stretchable panel exhibits a first color when in a substantially unstretched state, exhibits a second color when stretched within a first percentage range, and exhibits a third color when stretched within a second percentage range, the second percentage range being greater than the first percentage range;
wherein the stretchable layer comprises a polyolefin layer, wherein the polyolefin layer changes from the second color to the third color when the layer is stretched beyond a certain percentage.

19. An absorbent article as defined in claim 12, wherein the chassis defines a hip circumference and wherein the stretchable panel extends around the hip circumference.

20. An absorbent article as defined in claim 12, wherein the article comprises a diaper.

21. An absorbent article comprising:
a chassis defining a waist opening opposite two leg openings, the chassis comprising an outer cover, a bodyside liner, and an absorbent structure positioned in between the outer cover and the bodyside liner;
at least one stretchable and elastic panel associated with the chassis, the stretchable panel being positioned to stretch when the absorbent article is placed on a wearer, the stretchable panel changing color or undergoing a pattern change when the panel is stretched beyond a certain percentage indicating to the user that the article is approaching a size limit, the stretchable panel comprising a laminate having a gathered layer attached to a stretchable layer, wherein the stretchable layer comprises a film configured to polarize light, the film increasing in polarization when stretched causing a color change in the stretchable panel.

22. An absorbent article as defined in claim 21, wherein the polarizing film is transparent and is positioned over a colored layer.

23. An absorbent article as defined in claim 21, wherein the stretchable panel comprises a side region of the chassis.

24. An absorbent article as defined in claim 21, wherein the stretchable panel comprises a waist panel of the chassis.

25. An absorbent article as defined in claim 21, wherein the stretchable panel is elastic.

26. An absorbent article as defined in claim 21, wherein the film configured to polarize light comprises a polyurethane or a block copolymer that includes conjugated or aromatic groups incorporated into the polymer backbone.

27. An absorbent article as defined in claim 21, wherein the chassis defines a hip circumference and wherein the stretchable panel extends around the hip circumference.

28. An absorbent article as defined in claim 21, wherein the article comprises a diaper.

29. An absorbent article comprising:
a chassis defining a waist opening opposite two leg openings, the chassis comprising an outer cover, a bodyside liner, and an absorbent structure positioned in between the outer cover and the bodyside liner;
at least one stretchable and elastic panel associated with the chassis, the stretchable panel being positioned to stretch when the absorbent article is placed on a wearer, the stretchable panel changing color when the panel is stretched, the stretchable panel exhibiting a first color when in a substantially unstretched state, exhibiting a second color when stretched within a first percentage range and exhibiting a third color when stretched within a second percentage range, and wherein, when the absorbent article is worn by a user, the second color indicating that the absorbent article is in the correct size range for the user while the third color indicating to the user that the article is approaching a size limit; and
wherein the stretchable panel comprises a laminate having a gathered layer attached to a stretchable layer, wherein the gathered layer has a different color than the stretchable layer and wherein when the stretchable panel is in a substantially unstretched state, the color of the gathered layer predominates and wherein, when the stretchable panel is stretched, the panel changes color due to the color of the stretchable layer.

30. An absorbent article as defined in claim 29, wherein the stretchable panel is further configured to change color once stretched beyond a certain percentage.

31. An absorbent article as defined in claim 30, wherein the stretchable layer comprises polyethylene or polypropylene.

32. An absorbent article as defined in claim 30, wherein the stretchable layer comprises a polarizing film that increases in polarization when stretched.

33. An absorbent article comprising:
a chassis defining a waist opening opposite two leg openings, the chassis comprising an outer cover, a bodyside liner, and an absorbent structure positioned in between the outer cover and the bodyside liner, the chassis being elastic in at least the transverse direction, the chassis being configured to stretch when the absorbent article is placed on a wearer, the chassis being configured to change color or undergo a pattern change when any portion of the chassis is stretched beyond a certain percentage indicating to the user that the article is approaching a size limit;
wherein the outer cover of the chassis comprises a laminate having a gathered layer attached to a stretchable layer, wherein the gathered layer has a first color and the stretchable layer has a second color and wherein, when the chassis is in a substantially unstretched state, the color of the gathered layer predominates and wherein, when the chassis is stretched, the panel changes color due to the second color of the stretchable layer.

34. An absorbent article as defined in claim 33, wherein the stretchable layer comprises a polyolefin film that changes color when stretched beyond a certain percentage.

35. An absorbent article as defined in claim 33, wherein the chassis exhibits a first color when in a substantially unstretched state, exhibits a second color when stretched within a first percentage range, and exhibits a third color when stretched within a second percentage range, the second percentage range being greater than the first percentage range.

36. An absorbent article as defined in claim 33, wherein the stretchable layer comprises a polyolefin layer.

37. An absorbent article as defined in claim 36, wherein the stretchable layer comprises a polyethylene or polypropylene layer.

38. An absorbent article as defined in claim 35, wherein the stretchable layer comprises a polyolefin layer, wherein the polyolefin layer changes from the second color to the third color when the layer is stretched beyond a certain percentage.

39. An absorbent article as defined in claim 33, wherein the article comprises a diaper.

\* \* \* \* \*